(12) United States Patent
Babcock

(10) Patent No.: US 7,744,552 B1
(45) Date of Patent: Jun. 29, 2010

(54) PERSONAL UPPER BODY SUPPORT DEVICE FOR LOWER BACK MUSCLES ASSIST

(76) Inventor: Michael Anthony Babcock, 3124 Dakota Ave. South, St. Louis Park, MN (US) 55416-2057

(*) Notice: Subject to any disclaimer, the term of this patent is extended or adjusted under 35 U.S.C. 154(b) by 75 days.

(21) Appl. No.: 11/705,082

(22) Filed: Feb. 12, 2007

(51) Int. Cl.
*A61F 5/00* (2006.01)

(52) U.S. Cl. ........................................................ 602/19

(58) Field of Classification Search .................... 602/19, 602/23, 24, 28, 5, 1; 128/845
See application file for complete search history.

(56) References Cited

U.S. PATENT DOCUMENTS

| | | | |
|---|---|---|---|
| 406,663 A | 7/1889 | Mckinney | |
| 421,635 A | 2/1890 | Teufel | |
| 443,113 A | 12/1890 | Ray | |
| 654,173 A | 7/1900 | Mendenhall | |
| 703,477 A | 7/1902 | Russell | |
| 846,562 A | 3/1907 | Grayson | |
| 888,490 A | 5/1908 | Haas | |
| 903,403 A | 11/1908 | Quick | |
| 1,008,500 A | 11/1911 | Thorton | |
| 1,191,769 A | 7/1916 | Curts et al. | |
| 1,202,851 A | 10/1916 | Kelly | |
| 1,371,690 A | 3/1921 | Kelly | |
| 1,409,326 A | 3/1922 | Williamson | |
| 1,618,273 A | 2/1927 | Davidson | |
| 1,634,621 A | 7/1927 | Martinez | |
| 1,641,027 A | 8/1927 | Feaster | |
| 1,678,584 A | 7/1928 | Branson | |
| 1,812,529 A | 6/1931 | Haulbrook | |
| 3,029,810 A | 4/1962 | Martin | |
| 3,570,011 A | 3/1971 | Naig | |
| 4,010,744 A | 3/1977 | Boyen | |
| 4,608,716 A | 9/1986 | Brumfield | |
| 4,829,989 A | 5/1989 | Deamer et al. | |
| 5,127,897 A | 7/1992 | Roller | |
| 5,176,622 A * | 1/1993 | Anderson et al. | 602/19 |
| 5,199,940 A | 4/1993 | Morris et al. | |
| 5,259,833 A | 11/1993 | Barnett | |
| 5,709,648 A | 1/1998 | Webb | |
| 5,716,307 A | 2/1998 | Vadher | |
| 5,860,944 A | 1/1999 | Hoffman, Jr. | |
| 5,951,591 A | 9/1999 | Roberts | |
| 6,129,691 A | 10/2000 | Ruppert | |
| 6,450,131 B1 | 9/2002 | Broman | |
| 7,297,090 B2 * | 11/2007 | Torres | 482/74 |
| 2007/0236053 A1 * | 10/2007 | West et al. | 297/4 |

* cited by examiner

*Primary Examiner*—Kim M. Lewis
*Assistant Examiner*—Tarla R Patel

(57) ABSTRACT

A device that straps against the front of one's pelvis and features chest and leg engagements extending from a central main-body to create a personal upper body support system. As wearer bends forward from the waist, the leg engagements leverage oppositely threaded shafts to screw together into an internally threaded main-body either against a powerful spring means used to effect a compressive stop or a spring-back counter force to the wearer's overhanging upper body weight. A knob-ended threaded rod screws through one of the shafts to adjust the point of engagement and/or spring tension. This device creates a prop effect between the wearer's chest and upper legs. The oppositely threaded shafts provide a unique mechanism that divides the transferred load equally to each leg regardless of leg stance, as well as for allowing unrestricted upright walking.

16 Claims, 7 Drawing Sheets

PERSONAL UPPER BODY SUPPORT DEVICE FOR LOWER BACK MUSCLES ASSIST

BACKGROUND OF THE INVENTION

My invention relates to orthopedic and therapeutic devices worn to assist the musculoskeletal functions of the human body. More specifically, this device addresses several very common conditions of the lower back that can range anywhere between bothersome to life altering. The most common condition is simply low back muscle strain resulting from overuse. Continued abuse of these muscles often progress into much more serious injuries such as shifted vertebras and herniated discs that impinge on nerves. Nerve impingement is not only painful, but it can result in permanent damage that even surgery cannot fix.

Lower back injuries and degenerative conditions affect millions of people annually. Sadly, many of these statistics could have been prevented. But it is human nature to think it won't happen to us. So we keep abusing our backs until we can no longer tolerate the pain. By then, all too often it is too late for natural recovery; the damage is sometimes permanent. Surgery, having to change or quit our jobs (or both) is the end result for thousands. Back injuries in the workforce cost our nation billions of dollars per year. It is my hope that my device will offer a reduction in these unacceptable statistics.

Discovered Patents of Similarity mitted these due to their being either referenced in other patents that were similar to my device or because their listed descriptions suggested that they might be similar.

DESCRIPTION OF THE RELATED ART

Following an extensive search of prior patents, it became obvious that for years many different inventors have addressed this timeless issue of overworked back muscles. However, most of these arts relate to the methods of a body belt or restrictive fabric garments or harness that tightened lines or straps routed down the wearer's backside.

A few forms were designed with the same basic intention of redirecting the upper body's overhanging weight as my device does, however, the fashion in which they did this had various drawbacks that I will address. To simplify reviewing all of these patents (already listed above), I have regrouped them into the following four alphabetized categories:

A) Devices Most Similar
B) Bend-Restricting Harnesses
C) Body Belt & Garment Types
D) Other Referenced Patents (provided separately and not included in this specification)

The first category I will address will be from my "A" list. These are devices I considered to be most similar in function to my invention. All of the devices in this category transfer at least a portion of the user's upper-body weight to the fronts of

| | | | |
|---|---|---|---|
| 406,663 | J. D. Mekinney | Jul. 09, 1889 | Gardener's & Cotton Picker's Brace |
| 421,635 | J. Teufel | Feb. 18, 1890 | Bandage |
| 443,113 | R. Ray | Dec. 23, 1890 | Spring Body Brace |
| 654,173 | E. C. Mendenhall | Jul. 24, 1900 | Shoulder Brace |
| 703,477 | M. W. Russell | Jul. 01, 1902 | Body Brace |
| 846,562 | B. M. Grayson | Mar. 12, 1907 | Supporting Garment |
| 888,490 | G. W. Haas | May 26, 1908 | Flexible Corrective Brace And Corset |
| 903,403 | D. B. Quick | Nov. 10, 1908 | Shoulder Brace |
| 1,008,500 | H. C. Thornton | Nov. 14, 1911 | Back Brace |
| 1,191,769 | E. A. Curts et al. | Jul. 18, 1916 | Body Support |
| 1,202,851 | R. E. Kelly | Oct. 31, 1916 | Back Brace |
| 1,371,690 | R. E. Kelly | Mar. 15, 1921 | Back Brace |
| 1,409,326 | E. S. Williamson | Mar. 14, 1922 | Spring Lift for Stoopers |
| 1,618,273 | J. F. Davidson | Feb. 22, 1927 | Body Exerciser |
| 1,634,621 | I. Martinez | Feb. 23, 1926 | Device for Picking Cotton |
| 1,641,027 | A. J. Feaster | Oct. 09, 1926 | Brace |
| 1,678,584 | E. Branson | Jul. 24, 1928 | Body Brace |
| 1,812,529 | R. W. Haulbrook | Mar. 24, 1930 | Brace |
| 3,029,810 | V. L. Martin | Apr. 17, 1962 | Back Brace |
| 3,570,011 | C. B. Naig | Oct. 03, 1968 | Back Support |
| 4,010,744 | S. E. Boyen | Mar. 08, 1977 | Foot-Neck Harness Device |
| 4,608,716 | Brumfield | Sep. 02, 1986 | Sfty Jmp Suit Unifrm & Lftng Mchnsm |
| 4,829,989 | Deamer et al. | May 16, 1989 | Stoop Labr's Bdy Sprt Hvg Hng w/adj . . . |
| 5,127,897 | Roller | Jul. 07, 1992 | Therapeutic Back Support Device |
| 5,176,622 | Anderson et al. | Jan. 05, 1993 | Stoop Labor Assist Device |
| 5,199,940 | Moris et al. | Apr. 06, 1993 | Posture Training & Correcting Device |
| 5,259,833 | Barnett | Nov. 09, 1993 | Back Bndng Motion Limiting Apparatus |
| 5,709,648 | J. W. Webb | Jan. 20, 1998 | Resilient Back Support Device |
| 5,716,307 | Vadher | Feb. 10, 1998 | Body Exerciser Device |
| 5,860,944 | Hoffman, Jr. | Jan. 19, 1999 | Back Support Apparatus |
| 5,951,591 | Roberts | Oct. 14, 1999 | Back-Mounted Mobil Back Sprt Device |
| 6,129,691 | Ruppert | Oct. 10, 2000 | Pliant Bck Sprt Aprts w/Foot Engmnts |
| 6,450,131 | Broman | Sep. 17, 2002 | Forwrd Bendng Motion Cntrl Harness |

A separate list of other researched patents was enclosed with my submission entitle "My "D" list of Patents I concluded to be the least similar to my device". It was printed in landscape format in order to include a very brief description across from each. None of the patents contained in this list function like or resemble my invention. In fact, many of these have nothing in common at all with my device. I only subthe wearer's legs (as with my device). However, all of these lack the ability to distribute the transferred upper bodyweight equally to both legs if the legs are staggered. In a stance where one leg is forward of the other, these devices will loose much or all of their tension as well as causing the device to shift to one side. Also, these devices will either not engage while walking or interfere with the legs when attempting to walk.

One such device, the Williamson device, only engages with one leg. Additionally, none of these earlier devices appear to provide a means for readily altering bend limits or adjusting the resistance to bending. Most of these are very simple and basic, lacking the added functionability that my device offers. In addition, some of these are quite bulky and restrictive in regards to certain body movements. The following is my "A" list of "Devices Most Similar" beginning with the earliest:

| | | | |
|---|---|---|---|
| 406,663 | J. D. Mckinney | Jul. 09, 1889 | Gardener's & Cotton Picker's Brace |
| 443,113 | R. Ray | Dec. 23, 1890 | Spring Body Brace |
| 703,477 | M. W. Russell | Jul. 01, 1902 | Body Brace |
| 1,008,500 | H. C. Thornton | Nov. 14, 1911 | Back Brace |
| 1,191,769 | E. A. Curts et al. | Jul. 18, 1916 | Body Support |
| 1,202,851 | R. E. Kelly | Oct. 31, 1916 | Back Brace |
| 1,409,326 | E. S. Williamson | Mar. 14, 1922 | Spring Lift for Stoopers |
| 1,634,621 | I. Martinez | Feb. 23, 1926 | Device for Picking Cotton |
| 1,641,027 | A. J. Feaster | Oct. 09, 1926 | Brace |
| 1,812,529 | R. W. Haulbrook | Mar. 24, 1930 | Brace |
| 3,570,011 | C. B. Naig | Oct. 03, 1968 | Back Support |
| 4,829,989 | Deamer et al. | May 16, 1989 | Stoop Labr's Bdy Sprt Hvg Hng w/adj . . . |
| 5,176,622 | Anderson et al. | Jan. 05, 1993 | Stoop Labor Assist Device |
| 5,709,648 | J. W. Webb | Jan. 20, 1998 | Resilient Back Support Device |
| 5,951,591 | Roberts | Oct. 14, 1999 | Back-Mounted Mobil Back Sprt Device |

The Mckinney device is simple and straightforward. For a static position bend, if customized to a person using the proper tension flat or leaf springs, this could offer much benefit. However, this design lacks a means for adjusting the tension of the flat springs. This device would also inhibit walking while engaged and would rock back and forth while attempting to do so.

The Ray, Russell, Thornton, Kelly, Haulbrook and Webb devices can all be described, in function, similarly as the Mckinney device. The Curts device has no spring loading means, it only engages at a designed angle (bending) limit and no provisions are shown or mentioned for allowing the wearer to readily alter the stop (bending) angle.

The Williamson device, as already mentioned, uses only one leg (knee) to anchor the reaction of the flat spring concept. Another simple and straightforward device, but it too lacks adjustability and walk ability (when engaged).

The Martinez device appears quit bulky, restrictive and cumbersome.

The Feaster device is much more innovative. Its broadened usefulness is somewhat limited due to its forward protruding members while bent. For example, one could not use this to lean very close to anything, and this too would make it very difficult to walk, especially while bent forward.

The Naig teeter-totter styled device is prohibitively bulky in addition to the same walking (while engaged) restrictions. Furthermore, the foot anchor straps on this device pose tripping and entanglement hazards when walking. In addition, this is only affective with the legs locked straight at the knees. Bending at the knees would place an extra load for the quadriceps to resist I view the Deamer device as an improved version of the Curts device in so far as it has a spring loading effect rather than a stop. In addition, it offers some degree of adjustment. But again, this would interfere with walking and lacks the ability to equally divide it's loading to both legs. The Anderson device is another way of doing the same; it also lacks user adjustability.

Finally we come to the Robert device using a backpack type framework. Its upper end is tethered to a chest harness, its lower section anchors to the lower legs. This is similar to Naig's teeter-totter device, but this device uses elastic ropes and/or flexible shafts to provide a spring-type resistance. Sliding sleeves lock and unlock to switch between walking and bending support. There appears to be a lot of fabric pressing against the body that would be undesirable in hot environments. This device appears bulky and restrictive and would make squatting difficult.

Now I'll address my "B" list of "Bend-Restricting Harnesses:

| | | | |
|---|---|---|---|
| 654,173 | E. C. Mendenhall | Jul. 24, 1900 | Shoulder Brace |
| 846,562 | B. M. Grayson | Mar. 12, 1907 | Supporting Garment |
| 903,403 | D. E. Quick | Nov. 10, 1908 | Shoulder Brace |
| 1,371,690 | R. E. Kelly | Mar. 15, 1921 | Back Brace |
| 1,618,273 | J. F. Davidson | Feb. 22, 1927 | Body Exerciser |
| 1,678,584 | E. Branson | Jul. 24, 1928 | Body Brace |
| 4,010,744 | S. E. Boyen | Mar. 08, 1977 | Foot-Neck Harness Device |
| 5,860,944 | Hoffman, Jr. | Jan. 19, 1999 | Back Support Apparatus |
| 6,129,691 | Ruppert | Oct. 10, 2000 | Pliant Bck Spit Aprts w/Foot Engmnts |
| 6,450,131 | Broman | Sep. 17, 2002 | Forwrd Bendng Motion Cntrl Harness |

Basically all of these devices rely on a restrictive means such as straps (ropes, bungee cords, etc.) stretching up the back and fashioned to tighten when bending forward, thus relieving the duties of the lower back muscles. The lower portions of these devices anchor to the backsides of the wearer's feet or legs, while the upper portions anchor to either shoulder straps or the front side of a chest harness.

Although these forms of devices can be quit effective in-sofar-as relieving the lower back muscles, they all have at least a couple of basic design flaws. For one, all of these devices that anchor at the feet or ankle area will experience a loss of tension anytime the knees are bent. In addition, this tension would have to be fought by their leg muscles as soon as they unlock their knees.

But more importantly, all of the devices in this list impose a significant pulling force between the anchorage points, thus compressing the spinal column and its discs. This compression could inflict even further pain and injury to users already suffering from some forms of back conditions such as vertebral misalignments, compressed, bulging or herniated discs.

The last list I will cover in detail is my "C" list of "Back-Related Devices". This list covers a variety of devices, some relate to back bending aids and others intended for exercise. Everything in this list appears to have even less in common with my device as the Patents listed in my "A" & "B" lists. Nonetheless, they are worthy of mention. My "C" list is as follows:

The largest of my four categories, my "D" list, has been submitted separately and will not be addressed individually here.

SUMMARY OF THE INVENTION

Although an in depth patent search did uncover many devices that have addressed this timeless issue of sore backs resulting from extended or repeated bending, I believe my device is unique and improved. At the heart of my device is a compact differential mechanism that allows free opposing leg movements, as when walking, yet engages and divides the transferred upper-body weight equally to the fronts of both legs, regardless of their positions. Because my device's leg engagements contact the upper thighs; my device functions the same whether standing or kneeling thus providing its benefits during almost any activity.

| | | | |
|---|---|---|---|
| 421,635 | J. Teufel | Feb. 18, 1890 | Bandage |
| 888,490 | G. W. Haas | May 26, 1908 | Flexible Corrective Brace And Corset |
| 3,029,810 | V. L. Martin | Apr. 17, 1962 | Back Brace |
| 4,608,716 | Brumfield | Sep. 02, 1986 | Safety Jump Suit Uniform & Lifting Mechnsm |
| 5,127,897 | Roller | Jul. 07, 1992 | Therapeutic Back Support Device |
| 5,199,940 | Moris et al. | Apr. 06, 1993 | Posture Training & Correcting Device |
| 5,259,833 | Barnett | Nov. 09, 1993 | Back Bending Motion Limiting Apparatus |
| 5,716,307 | Vadher | Feb. 10, 1998 | Body Exerciser Device |

The Teufel device would not inhibit walking, as it does not engage with the legs. As a result, this device does little to assist the lower back muscles in supporting one's upper-body weight when bending forward. Its design purpose is that of helping hold one's back straight (as opposed to slouching) to assist with good posture.

The Haas device is also mainly designed for attaining and holding proper posture; it too will do little towards supporting a forward bend. The Martin device performs a totally different function. It was designed to give the spinal column a vertical lift (traction/negative pressure) by pushing between the arms, under the shoulders, (as with crutches) and the top pelvic region (hips). This also does not engage with the legs and is not designed to support a forward bend.

The Brumfield device covers many things, but in relation to my device, the suit basically incorporates a body belt and corset type of lifting assistance to the wearer. The Roller device consists of a stiff plate formed to mimic the lower back's curve. This is strapped against the lower back with belts around the waist and chest. This plate incorporates round bumpers that can be adjusted to put pressure on specified areas of the spine apparently to relieve disc pressure in the specified areas. This does not assist the lower back muscles during a forward bend.

The Morris device is another posture aid. It involves a pole strapped against the back and head. It does not assist the lower back muscles during a forward bend. The Barnett device is a harness with an adjustable elastic strap running up the back. This serves to restrict bending of the back (arching); this will do little to assist the lower back muscles when bending forward at the waist.

Finally we have the Vadher device that is designed to be an exercise harness/garment; it resists many movements. Any assistance this device might offer the lower back would fall under my restricting harness category. It shares very little in common with my device.

In addition, springs are incorporated within this differential mechanism that provide a gradient type of compressive resistance that can be altered quickly and easily. Through simply twisting a knob, wearers can dial-in the optimal amount of spring assist and/or the angle at which a bending limit engages. If desired, this spring-loading can be increased to a point where the stomach muscles are required to overcome the springs in order to bend over. In this situation, to return upright the stomach muscles would be relaxed and the springs would push the upper-body back to its upright position.

I designed this device with a receiver to accept a variety of upper-body engagement options to best accommodate various stomach and chest shapes. Although my device is normally best suited to be worn in front, minor alterations and the use of leg and chest straps can allow it to be worn on one's backside if preferred.

As most of these previous devices have not become popular, or even heard of, it would appear that there remained room for improvements. The challenge I accepted was to come-up with a compact lightweight spring loading device that would function close to the body. A device that allows necessary leg movements, even while bending forward. Better yet, to devise a mechanism that would evenly divide the load transferred to the legs, regardless of their positions, even during walking.

Once I came-up with this solution, I assembled an additional list of criteria that I felt was necessary to fulfill. Of course the primary requirement was that my device had to effectively prevent back strains, but I believed that satisfying the following list of additional criteria was crucial to warranting any further investment into this development. I felt it was additionally important that my device would:
  a) have a spring type loading or spring-back resistance to counter the upper-body weight rather than simply a stop
  b) provide for a full bending range of motion (180°)
  c) have an quick and easy means of adjusting such a spring loading mechanism
  d) allow normal and necessary body movements (especially the legs)

e) attach and detach from one's body in a quick and simple fashion
f) closely follow the body without bulky or grossly protruding parts
g) be comfortable, lightweight, durable and affordable
h) be adjustable to fit different sized and proportioned people
i) be unique enough to warrant a Patent I feel that my refinements have finally satisfied all of my additional criteria. My device is very effective at preventing back strains. It has a spring-loading mechanism with a side knob for quick and easy adjustment of its tension and where it begins to activate. Most normal body movements are allowed while wearing this device; one could even run or skate with this device on.

My device follows the body's contour close enough to mostly conceal it under loose clothing. It is more comfortable and much cooler than wearing a back-belt in warm environments. I have conducted extensive Patent searches and have concluded that my device is unique from all the Patents I discovered.

With its advantages over all the other Patents listed, my device lends itself to many useful applications. This device could help countless people perform activities that their backs may not otherwise tolerate. Some specific examples of these activities could include: shoveling, raking, gardening; brick/block laying, floor (or floor covering) installation, carpentry/mechanical work, utility workers, nursing assistants, surgeons, and assembly workers.

My device could be used in just about any activity where frequent and/or extended bending/leaning is encountered. This could even help employers and their Workers' Compensation insurance carriers. Hopefully some doctors will see it appropriate to prescribe wearing this device during their patients' recovery, thus allowing their patients to return to job duties that their backs would not otherwise be prepared to tolerate without such an aid.

While staying within the scope of the claims that follow, my device could be constructed in its simplest, thinnest and most lightweight form to serve only as an adjustable stop for leaning onto. On the other hand, it could be more elaborately constructed using a variety of compressive options. The compressive means I am currently using is that of stacked steel spring type (Belleville) washers.

Spring washers provide for easy customization of the spring tension by simply selecting the fashion in which they are stacked. They can be stacked in parallel, series or in a variety of combinations providing a wide range of tensions and travel lengths. Other means that will also work range from coil springs and elastomers (rubber-like materials) to compressed gases.

Leg and upper-body engagement members are made of lightweight aluminum and are adjustable to accommodate various sized users. Plastics, especially reinforced (as with fiberglass or carbon fibers), will also serve well as materials for many of these components. The upper-body engagement means can be fashioned in a variety of manners to best suit various stomach & chest shapes ranging from flat or paunch bellied to with breasts. I've made a variety of upper-body engagement attachments as options to best suit different situations and body shapes (FIGS. 9,10 & 11).

Currently the adjustable (telescopic) shaft 56 (FIG. 3) with a padded roller 51 at its upper end for rolling up and down the stomach/chest (as what happens while bending forward) seems to be the most versatile. Two vertical shafts 90 having a horizontal bridging member 92 in the form of webbing, fabric or a flexible plate either attached or stretched between them (as on the back of a beach or director's chair) also works well (FIG. 10).

For the ladies FIG. 11 a vertical track 130 (with two narrow padded backing plates 132) could be strapped against the chest (that runs up between the breasts) using an adjustable shaft 135 with a low-friction nylon guide 133 (attached at its upper distal end) that engages into the main-body's upper vertical receiver member that slides/tracks up and down during a bend (FIG. 11). The vertical track on the example built is attached to raised brackets from the padded plates using countersunk screws so as not to interfere with the slide mechanism. A stop means 131 is featured at its top end of the rail to prevent over travel thus de-railing.

Although my device is usually best suited to be worn on the front of one's body, simple modifications can enable it to be worn on one's backside.

BRIEF DESCRIPTION OF THE DRAWINGS

A detailed description of my invention follows with specific reference being made to the following list of figures in which.

DESCRIPTION OF THE PREFERRED EMBODIMENT

The overall operating function of my device is to assist, even relieve, the workload of the wearer's lower back muscles. This is accomplished through re-routing the wearer's overhanging upper body weight to the fronts of both upper legs. When breaking down the basic principles involved in accomplishing this, the external make-up of my device could be compared to a teeter-totter type lever, only more elaborate. A teeter-totter uses a central fulcrum; the fulcrum of my device is the saddle means and the belt.

The belt holds the saddle means, thereby the central horizontal tubular member of the main-body against the front of the wearer's pelvis. As the chest and legs apply opposing forces to the ends of this lever example, the belt pulls from the buttocks to hold the device from being pushed away. When enough force is applied to overcome the spring resistance, the lever bends at its center with a means to vary how much effort is required before it bends.

My device also has an internal mechanism that provides the engagement of resistance, whether abrupt (no springs) or compressive (with springs or etc.), and differential mechanism that allows opposing leg movements. This mechanism is an elaboration of a turnbuckle, a common hardware device often used with chains or cables to provide a means of adjusting their (pulling) tension on something.

A turnbuckle consists of a casting with hook-ended bolts (hook-bolts) threaded into each of its ends whereas one hook-bolt has right-hand threads and the other has left-hand threads. When these hook-bolts (representing the horizontal shafts of my device) are held from turning, rotating the casting (representing the main-body) in one direction screws the hook-bolts together whereas reversing the rotation screws them apart.

The vertical upper member(s) and upper-body engagement means on the device would be similar to fitting a wrench around the turnbuckle casting to leverage turning the casting against the resistance of the hook-bolts, whereas the vertical lower members or leg engagement members would be similar to engaging wrenches to the hook-bolts to either hold or turn them.

When the hook-bolts screw completely together, their inner ends jamb into each other causing an abrupt resistance. When this occurs, there exists a direct relationship between the amounts of force applied to rotate the casting, to the force required to hold the hook-bolts from rotating. An understanding of these basics will make it much easier to grasp the following more detailed descriptions of exactly how the inners of my apparatus works.

To further describe the principles that allow free opposing rotations/leg movements while simultaneously providing a spring resistance from any stance anytime the wearer bends forward, refer to FIGS. 4, 5, 6 & 7. These figures are simplified cutaway versions of the main-body's horizontal tubular member's inner workings.

Figure 4:
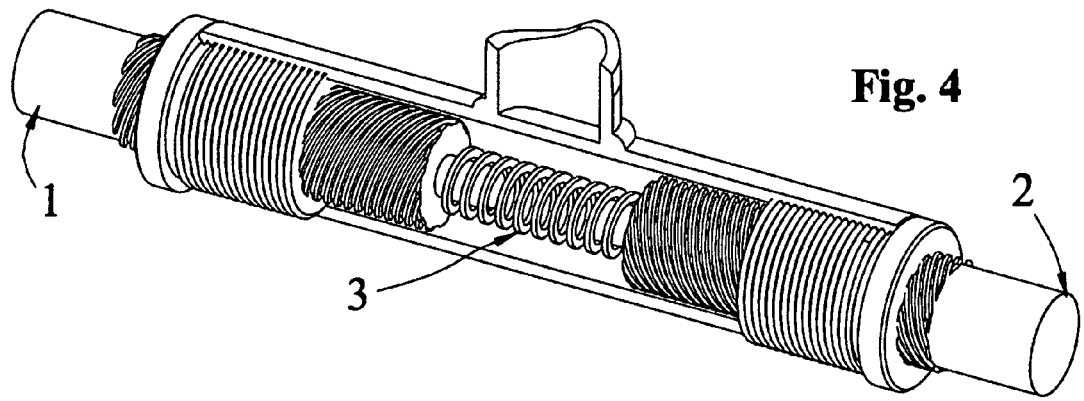
FIGS. 4, 5, 6 & 7 are simplified cutaway drawings depicting the main-body's horizontal tubular member, its left & right horizontal shafts and a coil spring representing its compressive means. These figures illustrate how the differential and compressive means mechanism functions.

FIG. 4 illustrates a neutral position as when the wearer's legs are together and is standing up straight. Note that the spring 3 (representing the devices compressive means) is not being compressed between the (simplified) shafts 1 & 2 (representing the device's horizontal shafts).

Figure 5:
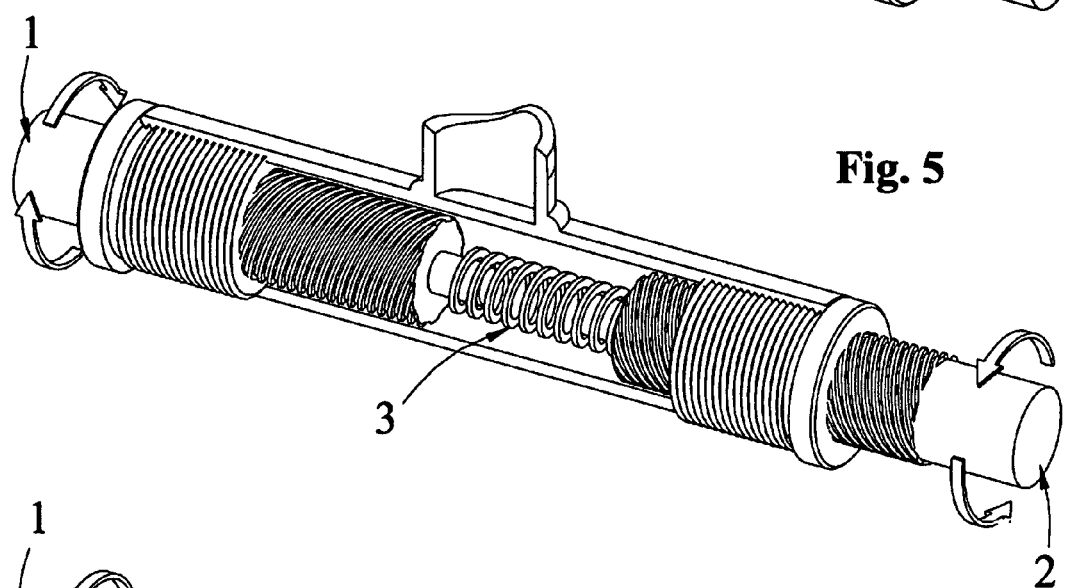

FIG. 5 illustrates what happens when the wearer walks. When stepping forward with his right foot, a forward movement of the right leg will push on the leg engagement's curved plate attached at the lower end of the right lower vertical member. This leverages a rotation to the shaft 1 as indicated. At this same time, the left leg would automatically move backwards and equal amount thus allowing an opposite rotation to the opposite shaft 2. As a result, as shaft 1 screws inward, shaft 2 simultaneously screws outward the same amount. This results in the spacing between the shafts to move to one side, thus nudging the spring 3 over with it, but without compressing it.

Figure 6:
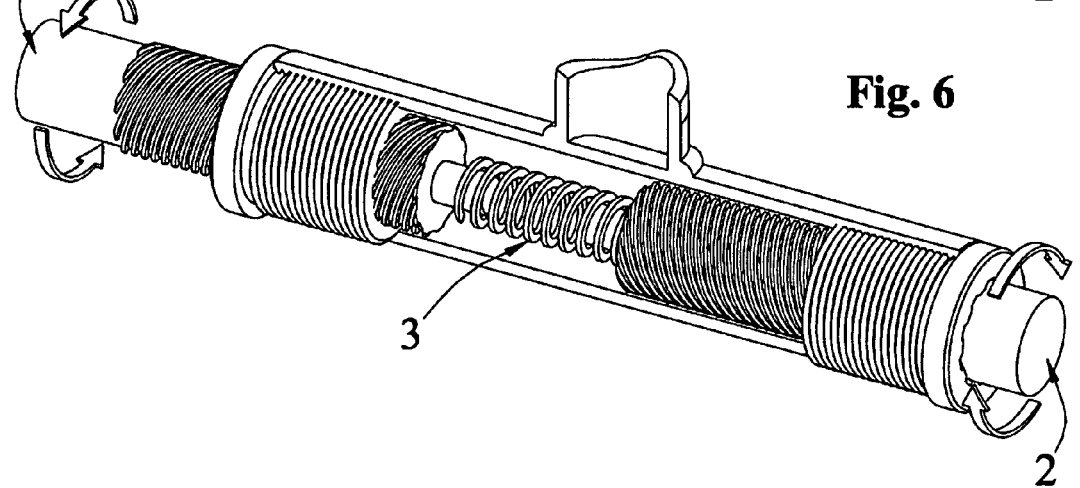

FIG. 6 illustrates what happens when the wearer now steps forward with his left foot. This also requires that the other leg move proportionately in the opposite direction. So the opposite happens in FIG. 6 as happened in FIG. 5. Now shaft 1 screws outward the same amount that shaft 2 screws inward. As the wearer walks, this action continues to repeat itself back and forth, leaving the spring uncompressed.

Figure 7:
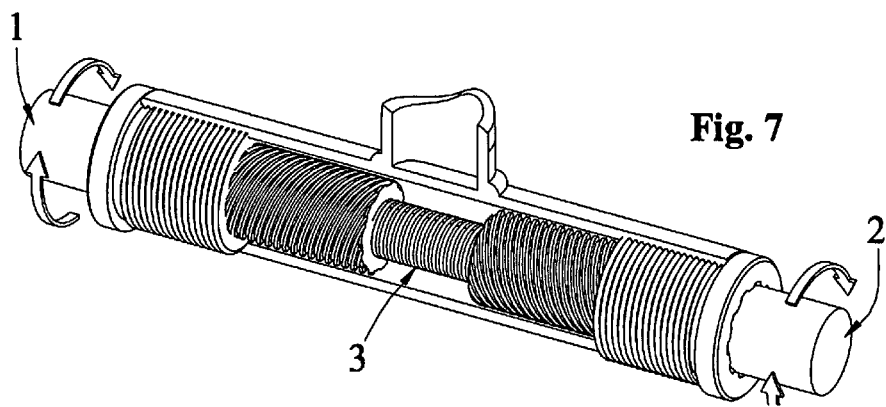

FIG. 7 illustrates what happens when the wearer stops walking and bends forward. When bending forward, both legs move towards the chest resulting in both shafts 1 and 2 rotating upward, thus screwing inward, thus compressing the spring 1, thus encountering the compressive resistance.

Regardless of which of these four illustrations you look at, you should now be able to see how the spring will compress from any of these positions as soon as both shafts rotate upward. Keep in mind that when bending, the main-body that houses these shafts rotates downward causing both shafts to screw inward. This is how the device can engage regardless of whether the wearer's legs are side by side or one in front of the other.

Figure 1:
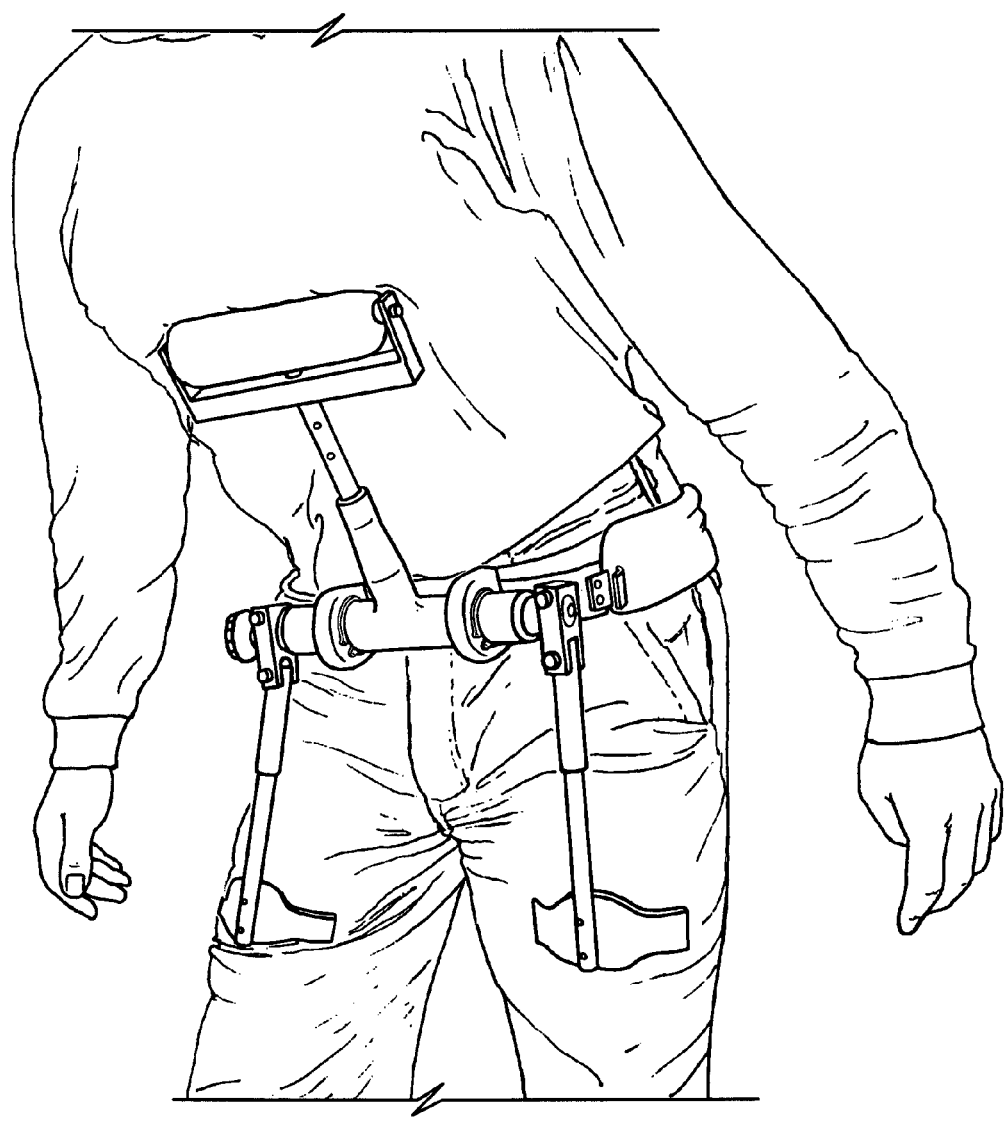
FIG. 1 is a partial view of a person wearing my device.
Figure 2:
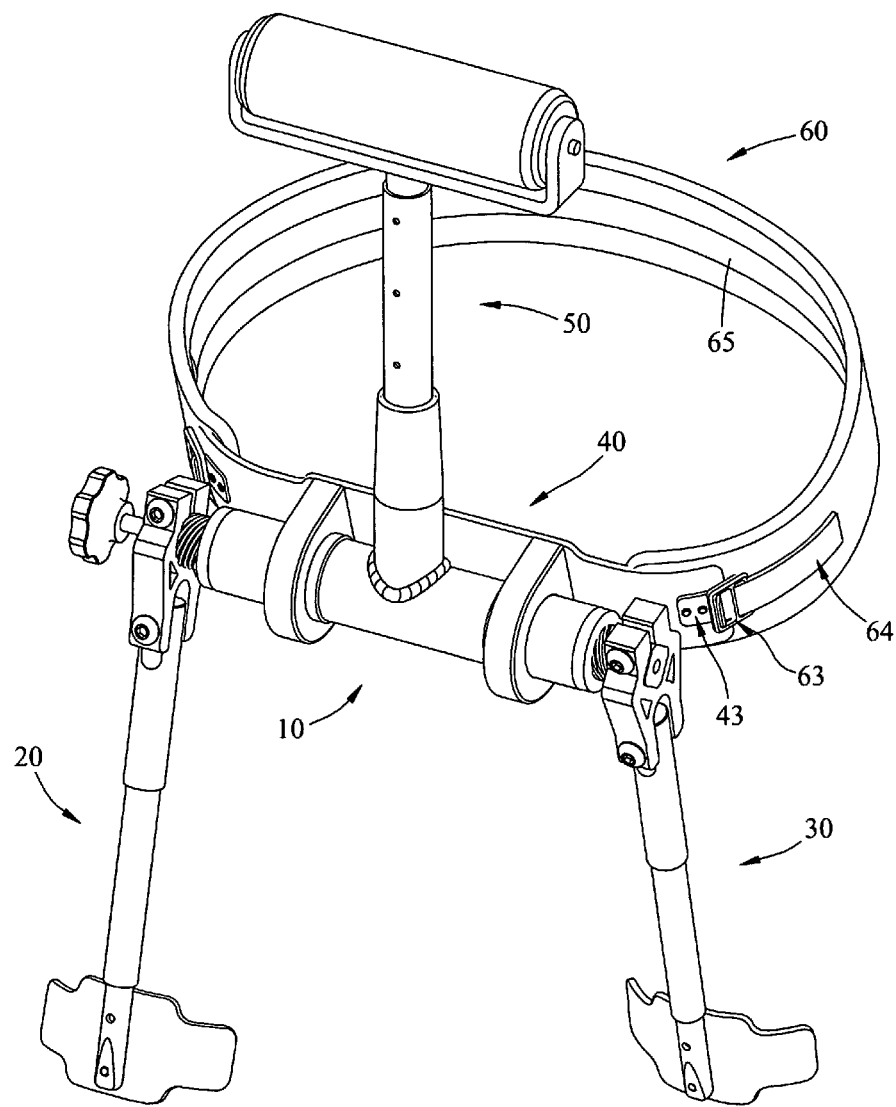
FIG. 2 is a view of the complete device, as though it were being worn, identifying its major components.

Now that the more technical aspects have been addressed, lets take an overview of this device in use. The following descriptions will be citing numbered parts identified in FIGS. 1, 2 & 3, whereas FIG. 1 is an illustration of the device being worn while supporting a forward bend, FIG. 2 is an illustration of the device by itself and FIG. 3 shows the main components separated from each other for clearer illustration.

Figure 3:
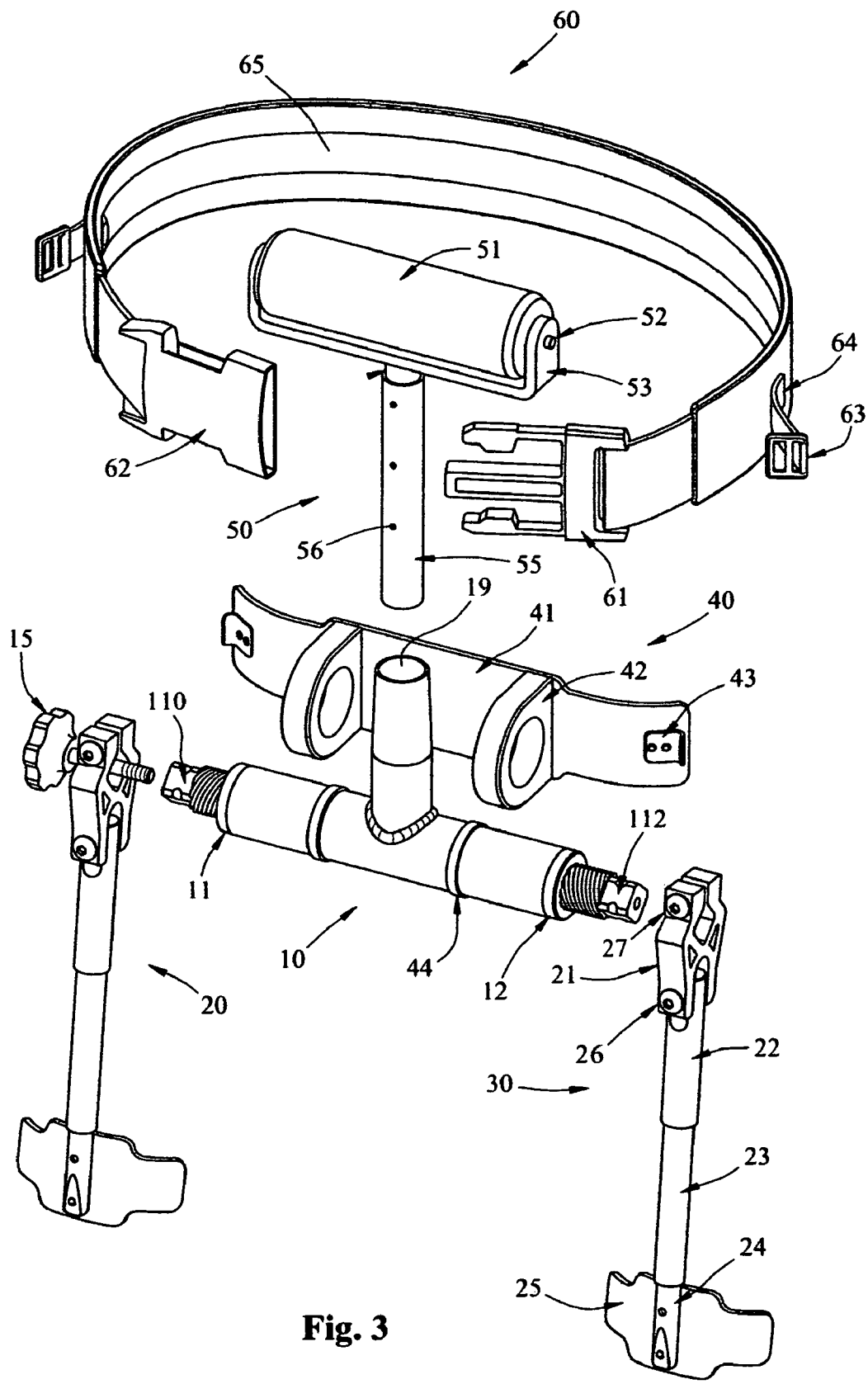
FIG. 3 is a partially exploded view of the complete device identifying all exterior components.

To use this device, one begins by first putting on and adjusting the belt assembly 60 that is best illustrated in FIG. 3. The belt is worn below the waistline, around the hips to encircle the buttocks just above its widest point. This prevents the belt from slipping down and loosening. This illustration shows a quick release buckle 61 and 62 to secure the belt assembly, although other readily available means can be used such as a loop & fastener system.

Within this belt assembly 60 is a sleeve 65 that slide-ably houses a secondary belt 64 with adjustable ring buckles 63 at its ends. With the belt assembly on, the device is brought into position and one of the two hooks 43 that, in this example, is located on the saddle means assembly's 40 saddle plate 41 and is engaged with a ring buckle 63. Then the other ring buckle is adjusted to snuggly pull over the hook on the opposite end of the saddle plate 41. This secondary belt 64 is what pulls and holds the device up against the wearer's body. As the device is used during bending, it wants to be pushed away from its wearer, a slight tug can be felt across the rear of the buttocks during a bend.

The saddle means assembly 40 (FIG. 3) is thereby detachably held to the belt assembly 60 whereas the main-body 10 is permanently, but rotatably, fastened to the saddle means assembly. My prototype uses two bored-out rigid nylon pieces as the saddle means 42 that slide over the round horizontal tubular member of the main-body 10 and stop at the two pressed-on collars 44.

The D-shaped saddles on this prototype 42 are screwed to the plate from its backside and must be fitted around the main-body before being attached to the plate 41. However, the entire saddle assemble can also be made of a fabric with straps wrapping around the horizontal tubular member of the main-body.

Once the saddle means assembly 40 is attached to the inner belt, via its hooks 43, it can be slid right or left inside the assembly's sleeve 65 to allow final centering of the device. Once adjusted, further attachment and removal of the device is quick and easy by simply pulling one of the buckles 63 forward on over its hook 43. This system makes it much easier than handling the entire device during the initial belt install and adjustment.

Figure 9:
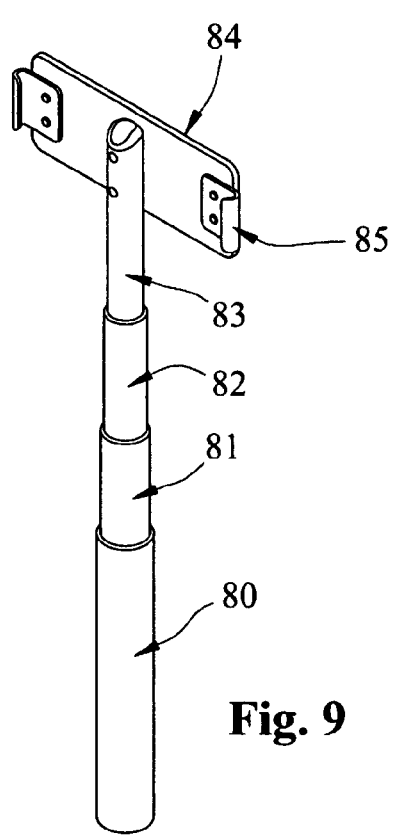
FIG. 9 shows an optional telescopic upper-body engagement means.
Figure 10:
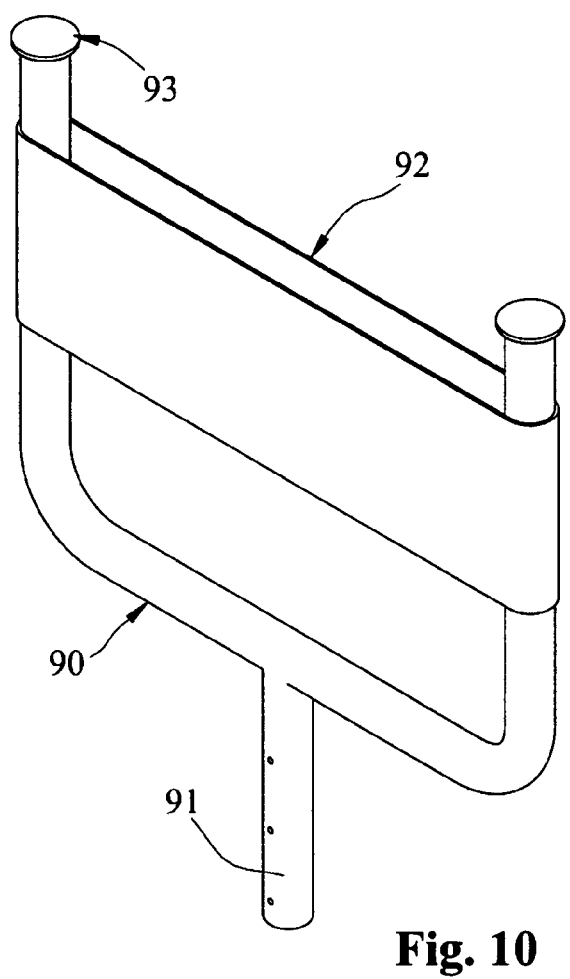
FIG. 10 shows an optional director's chair-back styled upper-body engagement means featuring a horizontal bridging member between two vertical upper members.
Figure 11:
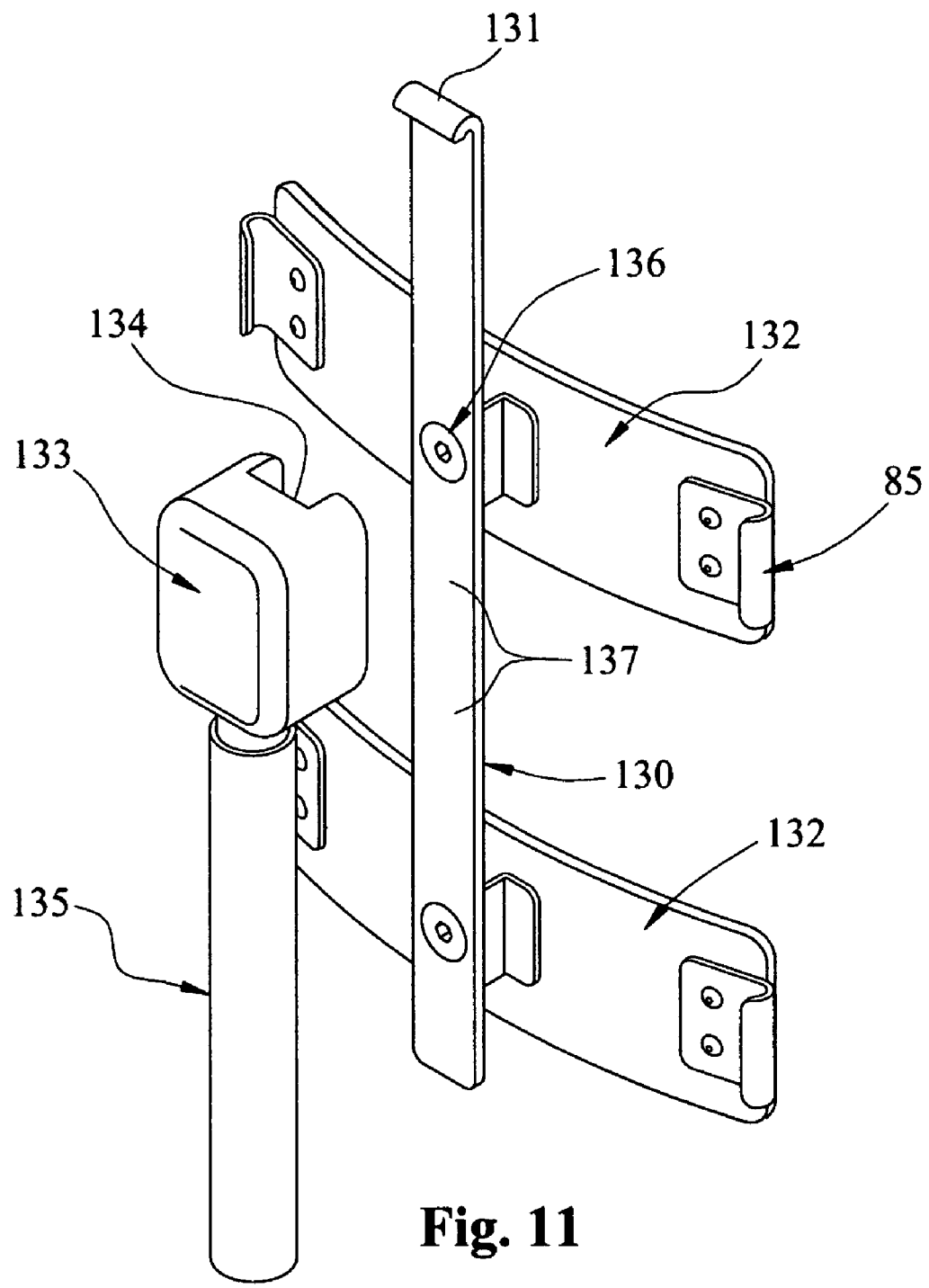
FIG. 11 shows an optional tracking guide and rail upper-body engagement means.

Extending upward from and attached at the general center of the central portion of the main-body 10 is a vertical upper member 19 having a bore to receive various forms of upper-body engagement means used to engage with the wearer's stomach and chest. FIGS. 1, 2 & 3 depict the roller version of an upper body engagement means and it's soft roller 51 (as identified on FIG. 3) that follows the stomach and chest while accepting its overhanging weight as the wearer bends forward. FIGS. 9, 10 & 11 illustrate other optional chest engagement means devised to use with this invention.

Also depicted in FIG. 3 we find two vertical members serving as the leg engagement members, 20 and 30 (right & left respectively). The leg engagements' upper distal ends are non-rotatably affixed to their respective horizontal shafts 110 and 120 via clamps 21 (and tightened by bolts 27) that secure to the shafts while attaching pivotally to the leg engagement members' upper sections 22 (via bolts 26 serving as the pivot means) in a fashion that allows for side movement of the wearer's legs. Both shafts 110 and 120 are forced to rotate in response to any forward or backward leg movements as well as being held from rotating when legs are stationary.

Curved contact plates 25 serve as the actual leg engagement means on this prototype and are attached to the lower distal ends of each of the leg engagement members 20 and 30 to center over and engage with the front upper portion of the wearer's legs. The contact plates 25 are curved enough that a slight spring tension holds these centered against the legs making strapping unnecessary. These contact plates can be fabricated from metal, plastic or similar.

Remember, the opposing threaded horizontal shafts 110 & 120 serve three important functions:

1.) they create the compressive resistance, or stop, during bending

2.) they provide the differential action that evenly divides the load to both legs 3.) they allow for non-engagement when walking For the following descriptions, keep in mind that all the illustrations are frontal views, resulting in the device's right side (in relationship to the wearer) being on the left side of the illustrations. With this in mind, in FIG. 3 the right leg engagement member (right lower vertical member) 20 attaches to the horizontal shaft 110 protruding from the (wearer's) right side of the main-body 10. The left leg engagement member (left lower vertical member) 30 attaches to the left horizontal shaft 120 protruding from the opposite end of the main-body. Shaft 110 has external left hand threads whereas the opposite shaft 120 has external right hand threads.

These shafts 110 & 112 are made from metal, but if made larger, it would make it possible to mold these from plastics or similar materials. The main-bodies of my prototypes have been made from aluminum (note the weld illustration where the vertical and horizontal member join) with brass inserts 11 & 12 serving as the threaded nuts that these shafts screw into. These threaded nuts have threads on their outside that engage into threads inside the main body 10.

A mold can be created that would allow the entire main-body housing to be cast as one solid piece, complete with it's internal threads for the shafts. This piece would be cast from plastic, aluminum, brass or other similar materials. This method would greatly simplify & lower high volume production costs of this part.

When bending over, the chest engages with the roller 51, or other optional upper-body engagement means attached to the vertical upper member 50, and leverages a forward rotation on the main-body 10 (like the earlier example of the wrench on the turnbuckle casting). This forward rotation of the main-body causes both shafts to screw together into a compressive means, such as springs, thereby creating the compressive resistance necessary to counteract the wearer's overhanging weight.

As the wearer bends further over, there becomes more overhanging weight to support, but there also becomes more compressive resistance to counter the increasing overhanging weight. As this compression increases, so does the pressure transferred to the upper legs. The more the chest presses on the upper-body engagement means, the more pressure is applied against the upper legs.

As the upper-body returns upright, the internal compression means forces the threaded shafts to screw apart from each other thus relieving or backing-off on the compression. A slight resistance is felt when walking with a forward load that is proportional to the amount of tension being maintained, however, without this tension, there is no appreciable resistance to walking at all.

A quick and easy means of adjusting the bend angle at which the springs begin to engage is incorporated. This is in the form of a knob-ended threaded rod 15 located at the wearer's right side emerging from the outer end of the threaded shaft 110. It is also used to adjust the tension experienced at a specific angle of bend.

Figure 8:
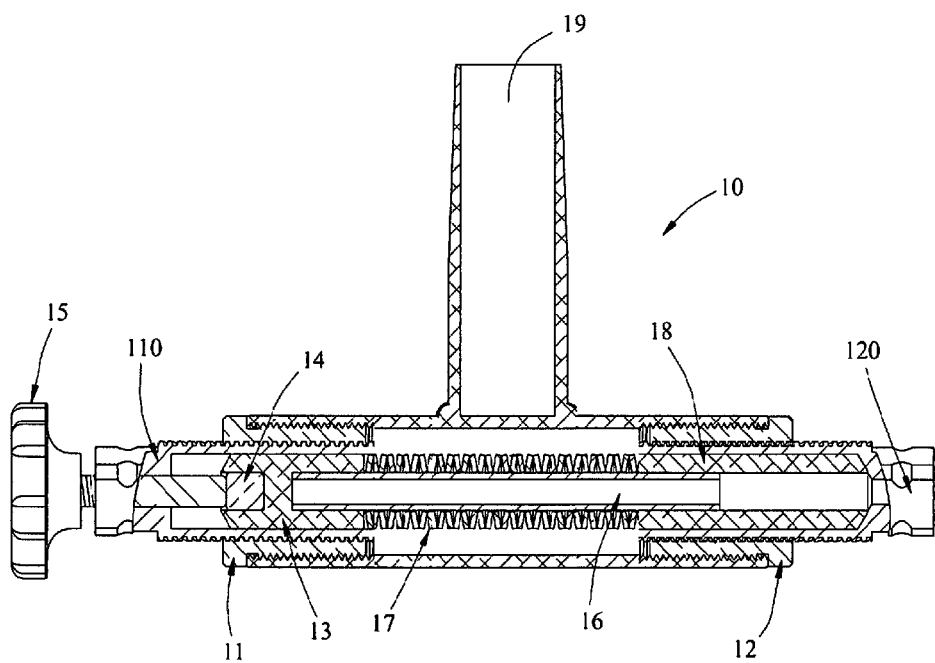
FIG. 8 is a detailed cut-away of the actual prototype's main-body and its internal parts.

FIG. 8 shows a more detailed cutaway view of my actual prototype main-body. The variable compressive means on this prototype is accomplished through the stacking of Belleville type spring washers 17 along a tube 16 that is supported between a plug 13 and a sleeve 18. The tube loosely fits into the bore of sleeve 18 that also loosely fits, but remains bottomed-out, in the bore of shaft 120. This sleeve affectively reduces the depth of the bore in shaft 120 and is what one end of the stacked spring washers press against.

At the same time, sleeve 18 allows the tube 16 to slide further in (without bottoming out) as the springs are compressed. As the springs rebound, the tube is allowed to slide back to its original depth within the sleeve. The inner distal ends of Plug 13 and sleeve 18 make direct contact with the stack of springs during compression.

The amount of spring washers used will vary according to the amount of compression that is desired. Spring washers have a unique quality that further makes them desirable towards this application. They can be stacked in series, parallel or in any combination of both to achieve a wide variety of tensions, progressive tensions and travel.

The overall assembled length of the springs, plug and sleeve (all contacting each other) must equal a length that will make contact between the bottoms of the bores in shafts 110 & 120 before any compressing can take place. Aluminum serves well for making the plug and sleeve, but other materials such as plastics could also be used. The length of sleeve 18 is easily altered to acquire the necessary overall length of the assembled stack of springs, the overall length referring to the outer distal end of plug 13 to the outer distal end of sleeve 18.

An adjustment means is accomplished through boring and internally threading the outer solid ends of either, or both, the threaded shafts 110 or 120. In this model the knob-ended threaded rod 15 screws into a threaded bore in shaft 110 and makes contact with a brass (nylon or other wear resistant material) piece 14 that is loosely fitted in the outer end of plug 13 that loosely fits in the bored-out center of the shaft 110.

Rotating this knob effectively changes the length of the plug 13 as if adding to or subtracting from its length. A quick twist of the adjusting knob 15 and the resistance is customized to the wearer's bending requirements. Screwing this knob in causes the springs begin to load earlier. One could even pre-load the springs before bending.

FIGS. 9, 10 & 11 illustrate optional upper-body engagement means devised to use with this invention. FIG. 9 represents a telescopic mast (tubes 80-82) whereas tube 80 fits into the main-body's upper vertical member 19 (identified in FIG. 3) thereby becoming an extension of the vertical upper member.

Tubes 81 & 82 and shaft 83 are fashioned to slide in and out (telescope). Plate 84, attached to shaft 83, presses directly against the chest if worn in front. If device were strapped on ones back side, hooks 85 can attach to a harness encircling the chest area to effect a pull on the chest harness to hold-up the upper body during bending.

FIG. 10 represents a chest cradling version that uses a horizontal bridging member 92 constructed of fabric or other flexible material that cradles the upper-body engagement area. Either two vertical upper members are required from the main body, or a Y design member 90 (as depicted in this FIG. 10) can be used to accommodate a main-body with only one vertical upper member.

Stem 91 would fit into 19 (of FIG. 3) to become one with it. The horizontal bridging member slides up and down (as depicted in FIG. 10) to accommodate an ideal upper-body engagement area while providing for changing lengths that occur while bending.

FIG. 11 represents a low-friction slide-track type of upper-body engagement means whereas tube 135 fits into 19 of FIG. 3 to become one with the main-body's vertical upper member. A slide block 133 in this example is attached to the upper distal end of vertical shaft 135 and is constructed of nylon.

In this example, slide block 133 contains a groove 134 that mates with the vertical slide rail 130 that is attached to plates 132 via flat head screws 136 countersunk into the face 137 of slide rail 130 altogether forming a rail assembly. A stop means 131 is included to prevent the slide block from exceeding its upper range and de-railing. An attachment means 85 is provided to accommodate straps if necessary to hold rail assembly against the chest area.

When being used, engagement pressure against the chest area is dissipated through the two plates 85. The main motivation and reason for this version of an upper-body engagement is to enable the rail assemblies support plates 85 to be designed and supported around a woman's breasts. The other upper-body engagement methods are not very breast friendly.

As for the block 133 being attached to the rail, spring tension provided by the device will hold the slide block on its mating track 130 while in use. Otherwise the slide block is part of the main-body's vertical upper member(s), and the rail assembly is separate from the device.

In conclusion, it is my belief that this device is improved, unique and useful over all previous arts.

What I claim is:

1. A personal upper-body support device configured to be worn by a person for reducing, even eliminating the stress otherwise imposed on the lower back muscles as a result from leaning or bending forward when worn, said personal upper-body support device comprising:
   (a) a belt assembly that is configured to be worn around hips of the person and encircle the buttocks, the belt having a quick release buckle to secure the belt about the hips, further including a sleeve and a secondary belt that is slidably received within said sleeve, said secondary belt having an adjustable ring buckle at its ends configured to pull and hold the device against the person's body;
   (b) a main body having a central horizontal tubular member having right and left distal ends, whereas its right distal end has left hand internal threads and its left distal end has right hand internal threads, a right shaft having mating external left hand threads screws partially into and extends from said main-body's right distal end and a left shaft having external right hand threads partially screws into and extends from its left distal end, wherein the inner distal ends of said shafts make contact either directly or indirectly through either a solid or compressive means when they screw together, and at least one vertical upper member provided at the central portion of and attached to said main-body;
   (c) an upper-body engagement means to engage with the person's chest or stomach, said upper-body engagement means is configured to be attached to said vertical upper member(s) to leverage a forward rotation of the main body;
   (d) saddle assembly having a saddle plate and two hooks, wherein the saddle assembly holds said main-body in a fashion that allows partial forward and backward rotation and is configured to position the main-body in cooperating relationship with the belt assembly when the saddle assembly's two hooks are engaged with the ring buckles of said belt assembly;
   (e) a right vertical lower member having upper and lower distal ends, wherein the upper distal end is non-rotatably affixed to the outer distal end of the right shaft extending from the right distal end of said central horizontal tubular member,
   (f) a left vertical lower member having upper and lower distal ends, wherein the upper distal end is non-rotatably affixed to the outer distal end of the left shaft extending from the left distal end of said central horizontal tubular member,
   (g) each of said right and left vertical lower members having a leg engagement member extending from the lower distal ends of said right and left lower vertical members for engagement with the front side of the person's upper leg areas, each of said leg engagement members having an upper and lower end;
   (h) a curved plate attached to each of the lower distal end of the leg engagement members configured to engage with the front upper portion of the person's legs, said plates are curved to provide a self-centering action against the legs making strapping unnecessary; and
   (i) a compressive means enclosed within the central horizontal tubular member of said main-body which allows for free rotation of said right and left shafts when walking and simultaneously providing a spring resistance when said right and left shafts rotate together in one direction when bending forward.

2. The personal upper-body support device of claim 1 wherein said vertical lower members each have a pivot means where they affix to the outer distal ends of said right and left horizontal shafts fashioned to pivot laterally.

3. The personal upper-body support device of claim 1 wherein the inner distal ends of said horizontal shafts are partially counter-bored to accommodate longer said compressive means.

4. The personal upper-body support device of claim 1 wherein said compressive means is a multitude of Belleville (spring) washers.

5. The personal upper-body support device of claim 1 wherein said compressive means is at least one wire wound compression spring.

6. The personal upper-body support device of claim 1 wherein said device incorporates at least one external adjustment means for quick and easy alteration of said compressive means and the angle at which a bending limit engages.

7. The personal upper-body support device of claim 6 wherein said external adjustment means is a knob-ended threaded rod screwing into at least one of the outer distal ends of said right or left horizontal shafts.

8. The personal upper-body support device of claim 1 wherein said vertical upper member(s) is one vertical upper member.

9. The personal upper-body support device of claim 8 wherein said one vertical upper member receives an upper-body engagement means that branches into two vertical members.

10. The personal upper-body support device of claim 1 wherein said vertical upper member(s) are two vertical members spaced apart and parallel to each other.

11. The personal upper-body support device of claim 10 wherein a horizontal bridging member is attached between said two vertical upper members serving as said upper-body engagement means.

12. The personal upper-body support device of claim 11 wherein said horizontal bridging member is of a flexible material.

13. The personal upper-body support device of claim 1 wherein said vertical upper member(s) is of a telescopic design.

14. The personal upper-body support device of claim 1 wherein said upper-body engagement means is a roller.

15. The personal upper-body support device of claim 1 wherein said upper-body engagement means is a low-friction slide that follows along a vertical track positioned against a wearer's stomach and chest area.

16. The personal upper-body support device of claim 1 wherein said attachment means for attaching to said saddle means are two hooks.

* * * * *